United States Patent [19]

Lester et al.

[11] 4,129,125
[45] Dec. 12, 1978

[54] PATIENT MONITORING SYSTEM

[75] Inventors: Robert W. Lester, Manhasset; Robert Hotto, New York, both of N.Y.

[73] Assignee: Camin Research Corp., New York, N.Y.

[21] Appl. No.: 756,026

[22] Filed: Dec. 27, 1976

[51] Int. Cl.$^2$ .............................................. A61B 5/00
[52] U.S. Cl. ............................. 128/2.05 R; 128/2 H; 128/2.05 T; 128/2.06 F; 128/DIG. 29; 73/344
[58] Field of Search .................. 128/2.05 R, 2 R, 2 H, 128/2.05 P, 2.05 T, 2.05 S, DIG. 29, 2.06 R, 2.06 F, 2.06 A, 2.08, 2 K; 73/344

[56] References Cited

U.S. PATENT DOCUMENTS

| 3,308,667 | 3/1967 | Pearlman | 128/2 H X |
| 3,572,322 | 3/1971 | Wade | 128/2.06 R |
| 3,638,642 | 2/1972 | Heflin, Sr. | 128/2.05 R X |
| 3,807,388 | 4/1974 | Orr et al. | 128/2.05 R |
| 3,863,626 | 2/1975 | Huber | 128/2.05 T X |
| 3,937,004 | 2/1976 | Natori et al. | 128/2.05 R X |
| 3,940,742 | 2/1976 | Hudspeth et al. | 128/2 R X |
| 3,978,849 | 9/1976 | Geneen | 128/2.05 T |
| 3,996,928 | 12/1976 | Marx | 128/DIG. 29 X |
| 3,999,537 | 12/1976 | Noiles | 128/2 R |
| 4,036,211 | 7/1977 | Veth et al. | 128/2 R |

Primary Examiner—Lee S. Cohen
Attorney, Agent, or Firm—Allison C. Collard; Thomas M. Galgano

[57] ABSTRACT

A portable system for monitoring the vital signs of a patient such as ECG, temperature, respiration, heart beat etc. consisting of a substantially flat housing having either exposed electrodes or temperature sensors for contact with the patient's skin. The device may also include one or more microphones for detecting respiration and heart beat. The device is preferably coupled to an elastic band which is worn around the patient's waist and in contact with his skin surface. The elastic band preferably has one electrode and the housing of the device contains the other ECG electrode. The measured vital signs are fed to a microprocessor or logic circuit which compares these vital signs with normal signs stored in a ROM memory. The measured vital signs are also stored in a RAM memory circuit and can be read out at desired time intervals. At the onset of any abnormal vital sign readings, an audible alarm will be triggered to warn of possible danger.

7 Claims, 7 Drawing Figures

PATIENT MONITORING SYSTEM

The present invention relates to an electronic device for monitoring the biological vital signs of a patient and detecting abnormal and dangerous state of such vital signs.

Due to the advances of modern preventative medicine, most fatal childhood diseases have been eliminated. Even today, however, there is still no answer to the precise cause of sudden infant death (SID), commonly referred to as "crib death". SID, which has been defined as the sudden and unexpected death of a previously healthy infant, is believed responsible for the death of 10,000 infants each year in the United States. It is the cause for approximately three deaths in every thousand births, and is the leading cause of death among infants between one week and one year of age. SID invariably occurs during sleep periods and is more apt to occur in later winter and early spring. It may be proceeded by a mild respiratory infection and is more common in socio-economically deprived areas than in middle class and upper class communities.

While the exact cause still remains a mystery, definite progress has been made in recent years and there is a growing body of evidence that victims of SID are not completely normal, that they have subtle physiological defects, probably in mechanisms that control breathing. Recent research studies have shown that the infants who die of crib death may be prone to frequent and prolonged periods of apnea (cessation of breathing) during sleep. As a result, various doctors have been conducting sleep tests on babies wherein the infant's vital signs (i.e., temperature, heart beat, respiration etc.) are continuously monitored and recorded in order to determine whether the baby is prone to long periods of sleep apnea, as well as to study episodes of sleep apnea an its effects on heart rhythm, respiratory reflexes and pathological changes in the subject.

In those instances where infants were found to have a high risk of prolonged sleep apnea, the doctors are now recommending that the infant be sent home with the monitoring equipment, instructing the parents on how to use them and what to do if the baby should stop breathing. However, the monitors themselves, which are primarily designed for use in hospital intensive care units, can be quite expensive, complicated and difficult to use. In addition, this electronic equipment requires the use of sensors for each of the vital signs monitored which must be taped to the body of the subject and which are wired to the monitor readout or recorder. As can be appreciated, use of such monitoring equipment whether for hospital or home use, is most uncomfortable to the patient. While various attempts have been made to eliminate these drawbacks, so far as is known, no presently-available monitor has effectively dealth with all of these problems in a sufficiently simple manner.

Accordingly, it is an object of this invention to provide a novel device for measuring, monitoring and recording the biological vital signs of a patient.

It is also an object of this invention to provide such a novel device which also analyzes and detects abnormal and dangerous states of the patient's vital signs and which triggers an alert signal or alarm in response thereto and which further indicates which vital sign is effected.

It is a further object of this invention to provide such a device which is relatively simple to use, inexpensive and reliable in operation.

It is an additional object of this invention to provide such a device which may be conveniently and comfortably worn by the patient and which eliminates the need for taping wired sensors to the patient's body.

It is a more particular object of this invention to provide a novel device having the foregoing attributes and features which is especially suitable for monitoring the vital signs of an infant in a home environment.

Accordingly, the present invention provides an electronic monitoring device particularly suitable for babies, which is capable of continuously monitoring the patient's heart beat rhythm, breathing rhythm and temperature. If any of these vital signs falls into a critical condition, the electronic monitor will alert personnel by sounding an alarm and activating a display indicating what the problem is. The electronic monitor analyzes the vital signs of the patient by use of a microcomputer in order to detect a problem. After noting a problem which occurs for a period longer than normal, such as 10 seconds, the unit will activate an alarm. The delay feature is to permit the unit to determine if a problem is actually critical or just a minor problem such as a momentary cough.

The electronic apparatus of the present invention includes a temperature sensor composed of an ordinary digital thermometer interfaced to a microcomputer. There is also at least one microphone sensor which senses the sound activity of the heart rhythm and the respiration rhythm in order to determine cardiac and respiratory status. A preferred unit includes two microphones separated from each other for measuring the above functions.

The electronic monitor of the present invention also includes a memory unit which will record each of the vital signs every hour for a future readout.

The apparatus of the invention is preferably in the form of a belt having a buckle which houses the computer and memory. The unit is turned on by closing the belt into the buckle around the body of the patient. Should any of the patient's vital signs become abnormal, the electronic device after a short delay, will sound the alarm alerting personnel near the patient that a failure has taken place. This will give persons near the patient ample opportunity to act on the patient in an attempt to restore breathing or other vital signs.

Other objects and features of the present invention will become apparent from the following detailed description considered in connection with the accompanying drawings which disclose the embodiments of the invention. It is to be understood however that the drawings are designed for the purposes of illustration only and not as a definition of the limits of the invention.

In the drawings wherein similar reference characters denote similar elements throughout the several views.

Figure 1:
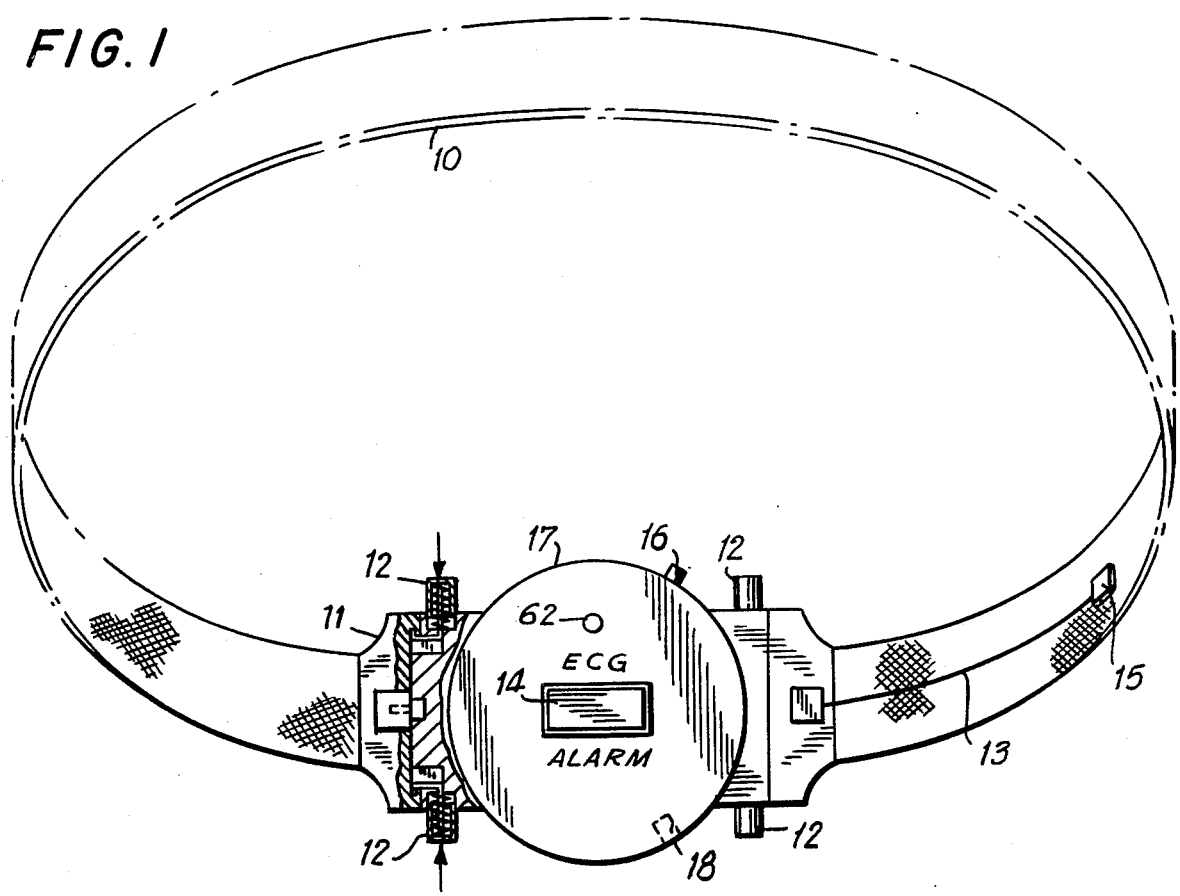
FIG. 1 is a perspective view of the electronic monitoring device for attachment to a patient.

Referring to FIG. 1, there is shown an elastic belt or strap 10 which is designed to fit around the patient's chest or stomach area. The right side of the belt is shown twisted so that the back side of circular housing 17 may be illustrated. Housing 17 is connected to the belt by means of spring loaded pins 12 which contain L-shaped hooks which grip connecting flanges 11 which are secured to each end of the belt. On the left side of the drawing there is also provided a microswitch so that when belt 10 is connected by means of flange 11 to housing 17, the electronic circuitry within housing 17 becomes activated for sensing vital body signs. Housing 17 is preferably constructed in the form of a flat circular disk and includes a metal plate 14 which protrudes slightly from its surface to make contact with the skin of the patient. A second metal electrode 15 is disposed on the surface of the belt to also make body contact. A wire 13, which is insulated and may pass through the center of the belt connects back through the belt coupling into housing 17 so that the two metal electrodes form the basis of an ECG measuring unit. Belt 10, couplings 11, and housing 17 are otherwise preferably constructed of non-conducting material such as plastic, nylon and the like.

Housing 17 also includes an alarm turn off button 16 so that if a vital sign should fail and the alarm is sounded depressing button 16 will shut the alarm off and reset the circuit. Adjacent to metal plate 14 is also included a blinking light 62 which indicates that once the belt is connected to the housing, that the electronic circuitry is functioning and measuring the patient's vital signs. Lamp 62 is preferably a LED (light emitting diode). The belt coupling on the right hand side of housing 17 which includes wire 13, additionally includes a connector (not shown) to electrically connect wire 13 into the electronic circuitry of housing 17. Housing 17 also includes a receptacle 18 for receiving a plug so that stored memory information concerning the measured vital signs of the patient can be read out on an instrument such as a paper tape printer.

Figure 7:
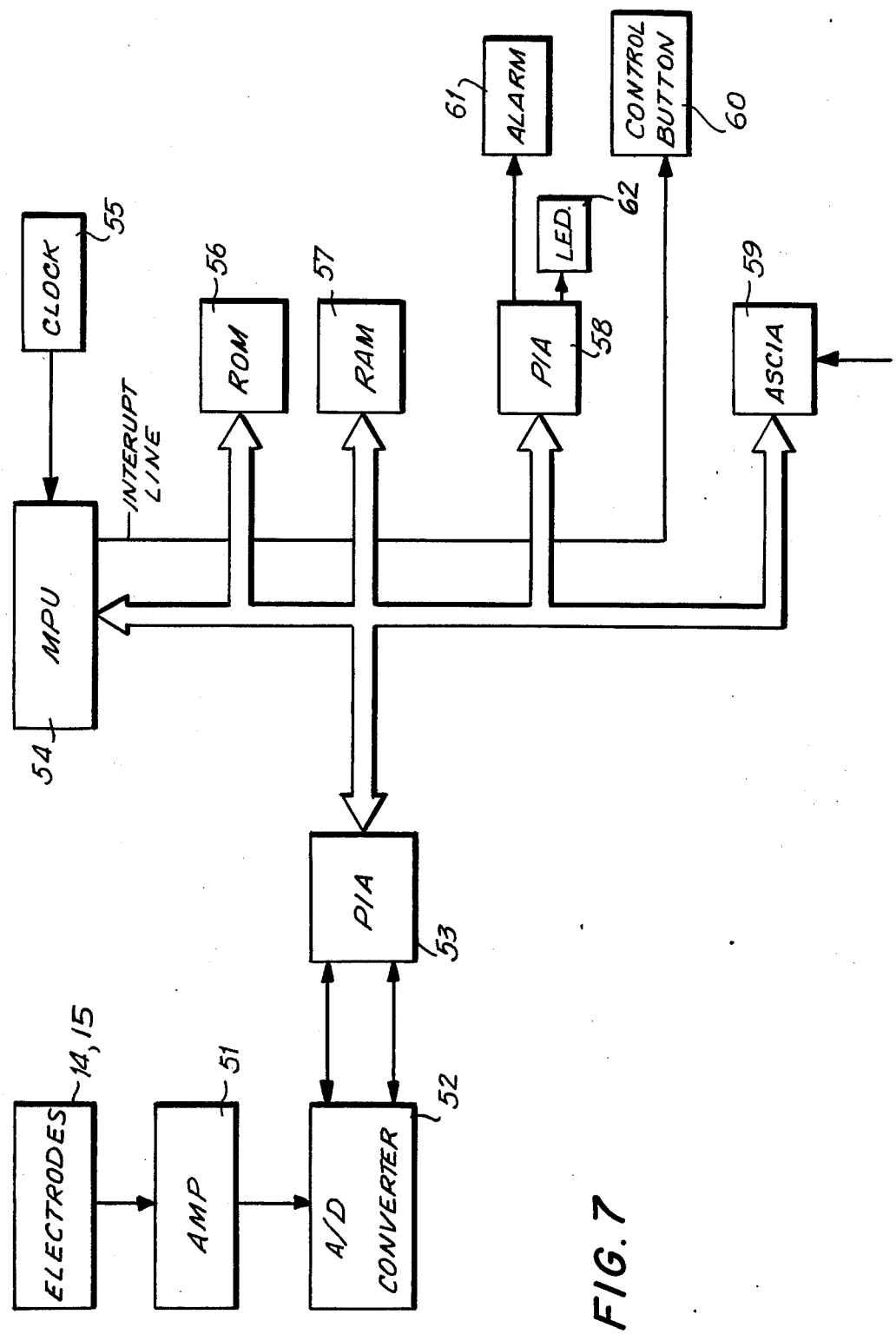
FIG. 7 is an electronic block diagram for the apparatus of FIG. 1.

Referring to FIG. 7 there is shown an electronic block diagram partly in schematic form of the electronic circuitry of the apparatus of FIG. 1. Electrodes 14 and 15 which represent the ECG electrodes in contact with the skin of the patient are coupled through amplifier 51 to an analog/digital converter 52 where the ECG information is converted to digital information and fed into a peripheral interface adapter (PIA) 53. The electrodes are designed to monitor the three major cardiac wave forms (P-wave, QRS complex and T-wave) from the voltage fluctuations appearing in two separate skin areas as the heart muscle expands and contracts.

A microprocessor unit MPU 54 which is fed by a digital clock or oscillator 55 is coupled to ROM circuit 56, RAM circuit 57 and peripheral interface adapter PIA 58 is connected to an alarm 61 and lamp 62. Control button 60 is used for resetting the circuit and is coupled to MPU 54. Microprocessor 54 is also connected to ASCIA 59 which is an interface for a telephone or telegraph network so that information stored in the microprocessor can be fed out serially.

Clock 55 is preferably a quartz crystal oscillator having a 1 mhz output. Clock 55 thus allows the microprocessor 54 to keep track of the precise time during measurement of the patient's vital signs. Random access memory (RAM) 57 is a read-write memory wherein the binary digits within the memory can be changed as well as read by the microprocessor computer. RAMs are manufactured by Itel Corporation (2102) or National Semiconductor Corporation (MM2101-1 or MM2101-2). Read-only memory (ROM) 56 is a semiconductor memory where it is not possible to change the state of the binary digits in the memory. The memory is put in when the ROM is manufactured so that it can be read but not changed. Microprocessor unit 54 is an indefinite variety of logic devices implanted in an intergrated circuit. This integrated circuit is composed of a chip of processed silicon wafer and is usually mounted in a dual inline package (DIP). The microprocessor can be considered a digital computer. This is because of the similarity of instruction sets, addressing modes and execution speeds between the processors and computers. Available mircoprocessor units are manufactured by Intel Corporation (8080) and National Semiconductor Corporation (SC/MP 8080, and IMP/16).

The patient monitoring system of the present invention can be programmed in a manner similar to an ordinary computer. The systems program is stored in ROM 56 so that the microprocessor can analyze the cardiac rate produced by electrodes 14 and 15. In a typical computer program which requires 320 samples per second, the three major wave forms, the P-wave, the QRS complex and the T-wave are analyzed and compared with the information stored in the memory. Through a cardiac sub-routine, the processor finds the beginning and end points of the three basic wave forms. The wave form analysis is designed to give a minimum number of parameters that fully characterize a patient's danger point. The processor in the present invention is preferably designed to analyze one vital sign for approximately two consecutive minutes before switching to another vital sign.

The ECG signals which are picked up by electrodes 15 and 14 and amplified by amplifier 51 are converted to digital form by means of A/D converter 52. The microprocessor 54 then filters out the ambient pulses which are the result of muscle movements etc. The signals are analyzed by means of the software routine as to how the heart pattern should be in accordance with the three types of wave forms. If the signals are out of line with the program, microprocessor 54 will consider the patient to have an abnormal heart state and will enable alarm circuit 61 to indicate patient heart trouble. The unit will also record this abnormal reading in read-write memory RAM 57. The alarm is deactivated by depressing the control button 60 which resets the program and allows the microprocessor to start working again after one minute. The alarm 61 is preferably a solid state electronic beeper.

ASCIA circuit 59 is an interface circuit which is designed to serially put out the information stored in RAM 57 so that the information can be fed over the telephone lines to a central computer or a hospital or a printer.

Figure 4:
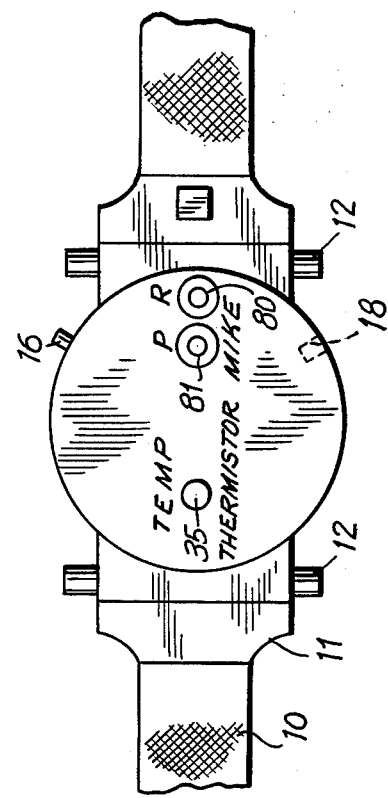
FIG. 4 is a further embodiment of the electronic monitor of FIG. 3.

FIGS. 2, 3, 4, 5 and 6 disclose another embodiment of the invention for measuring additional vital signs of the patient. Housing 17 is also provided with a display for indicating the pulse, the temperature and the respiration of the patient. These displays are preferably liquid crystal (LCD) displays which are mounted on the outside surface of the housing so that they are visible to a nurse or outside observer while the patient is resting. On the inside of housing 17 in contact with the body as shown in detail in FIG. 4 is a temperature sensor 35 preferably in the form of a thermister and at least one microphone sensor 81. It is preferably to include a second microphone 80 so that both the pulse "p" and the respiration "R" can be measured separately instead of in a single microphone unit.

Figure 3:
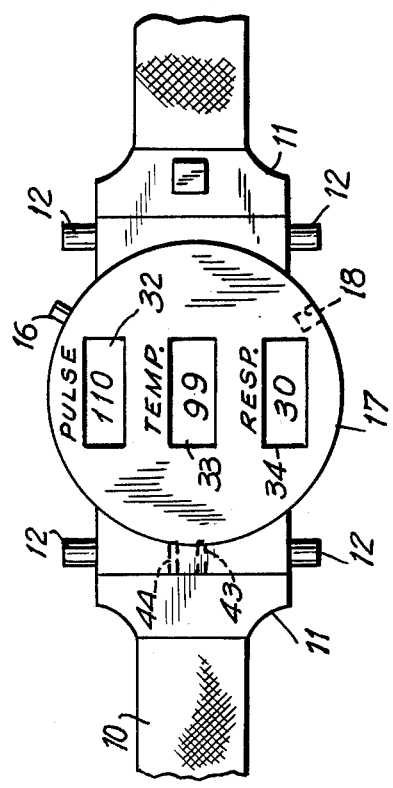
FIG. 3 shows another embodiment of the electronic monitor of FIG. 1.
Figure 5:
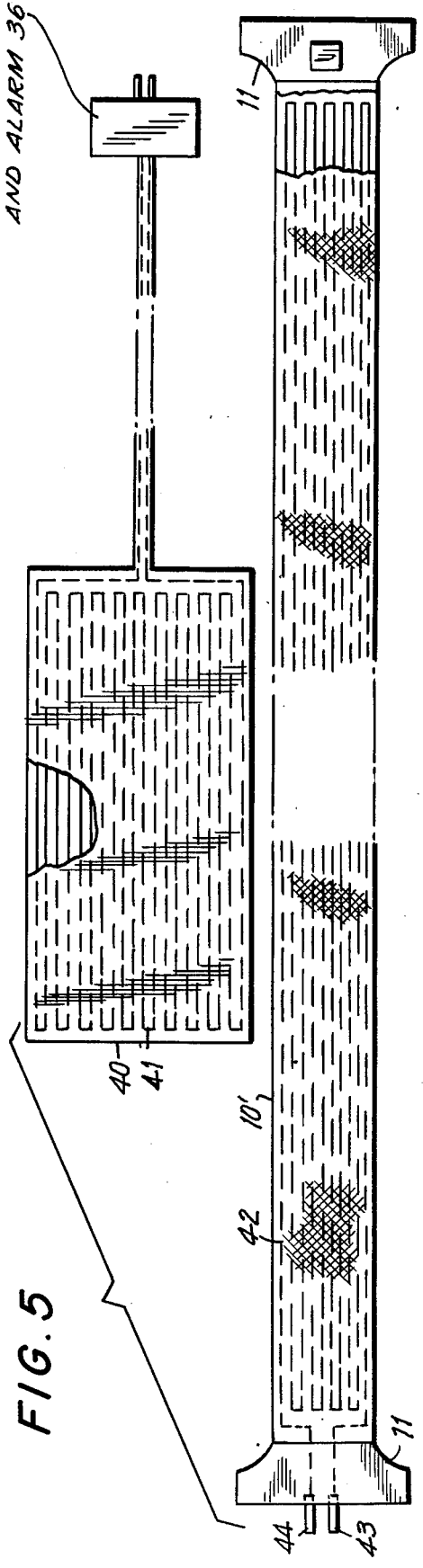
FIG. 5 is a perspective view of an induction coil and receiving unit in combination with a transmitting and receiving antenna system for the apparatus of FIGS. 1, 3 or 4.

FIG. 5 discloses a combination power induction unit and transmitting receiving unit as an alternate embodiment to the invention. A substantially rectangular induction coil mat 40 having a grid of wires 41 are preferably powered from a low voltage transformer and alarm circuit 36 which plug into ordinary household power. Mat 40 is preferably placed underneath the bedding of the patient so that it will create a magnetic field in the area where the patient is sleeping. In a similar manner, belt 10' is provided with serially connected wires 42 in the form of a large induction coil so that it is capable of picking up the AC field radiated by mat 40. The induced voltage of belt 10' is connected through terminals 44 and 43 and connection flange 11 into housing 17 as shown in FIG. 3 by the broken lines. Thus, the apparatus is self-powering through the mutual inductance between pads 40 and belt 10', and either no batteries are needed to power the unit, or only a small standby battery is needed to stabilize the power provided to the unit.

The apparatus of FIGS. 3 and 4 may also be provided with an RF transmitter for transmitting the vital sign information such as temperature, respiration rate, and pulse through terminals 43 and 44 in belt 10' so that the information can be picked up by induction coil 41 in pad 40. Transformer 36 thus also becomes an RF receiver and includes an alarm which will sound when any of the vital signs become abnormal.

Figure 6:
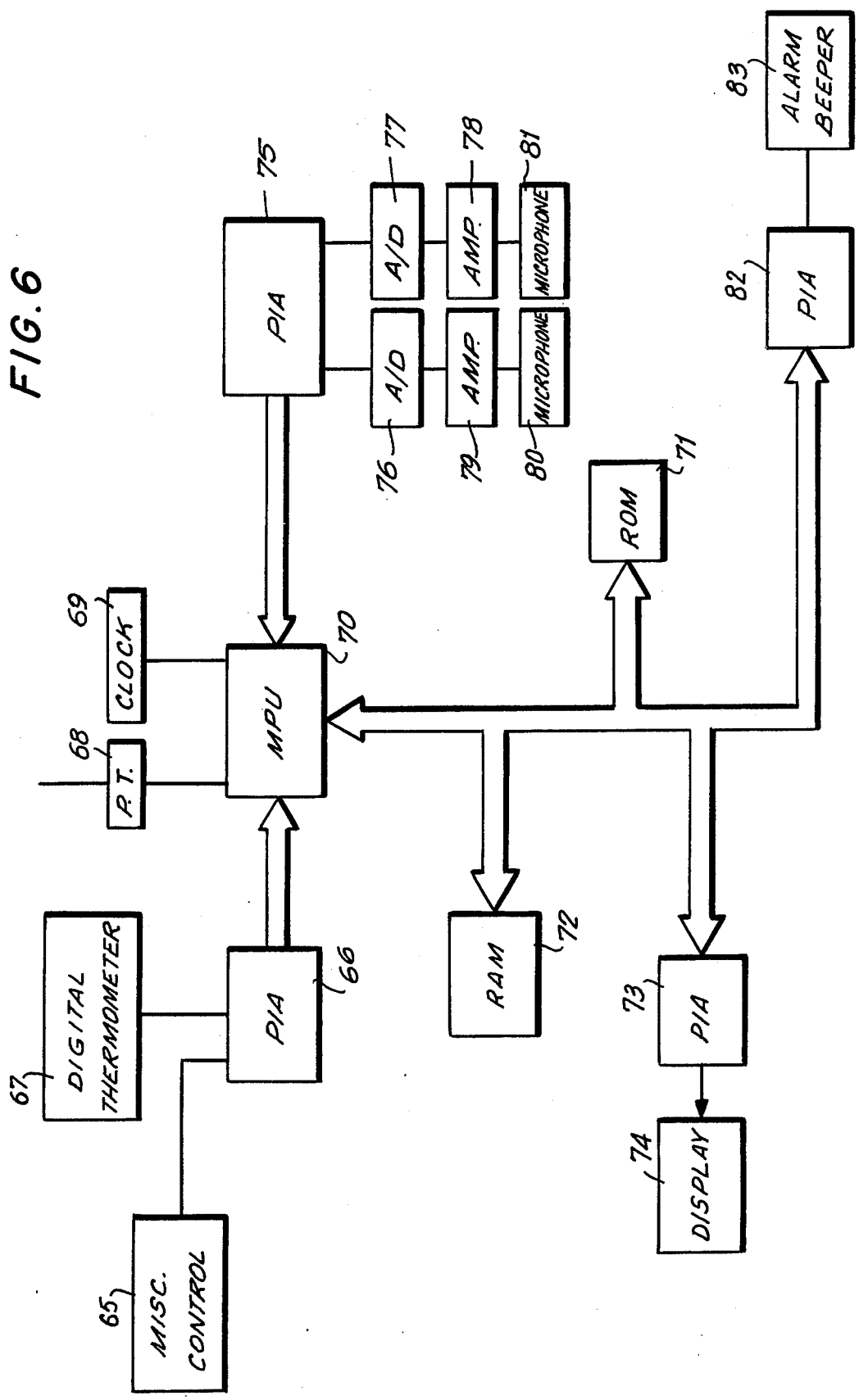
FIG. 6 is an electronic block diagram suitable for the apparatus shown in FIG. 4.

The embodiments of FIGS. 3 and 4 utilize an electronic circuit as illustrated by the block diagram of FIG. 6. The heart of the system is a microprocessor MPU unit 70 which is driven by a clock oscillator 69 and a programmable timer 68. The programmable timer, which interrupts microprocessor 70 performs a clock function needed for real time measurements. The microprocessor keeps count of the interruptions coming from the programmable timer and therefore keeps track of the precise time. The circuit of FIG. 6 also includes a digital thermometer 67 which is connected through a peripheral interface adapter 66 to microprocessor 70. A miscellaneous control circuit 65 may also be included so that abnormalities or peculiarities of the patient may be included in the program. A second peripheral interface adapter PIA 75 is connected to microprocessor unit 70. Microphones 80 and 81 which are designed to sense respiration and pulse respectively, are coupled through amplifiers 79 and 78 and analog to digital converters 76 and 77 so that both pulse and respiration can be fed into microprocessor 70 through PIA 75. Microprocessor unit 70 is also coupled to ROM 71 which is fixed memory, and contains the system program consisting of a number of instructions telling the microprocessor system 70 how to analyze the pulse, temperature, and respiration information which are collected by digital thermometer 67 and microphones 80 and 81. RAM 72, which is a scratch pad memory, is also connected to microprocessor unit 70 for storing the vital information which is measured sequentially. Display 74 which is connected through peripheral interface adapter 73 to microprocessor unit 70 provides the display readings at display outputs 32, 33 and 34 of FIG. 3. A further peripheral interface adapter 82 connected to microprocessor 70 is coupled to alarm beeper 83 for sounding an alarm when an abnormal vital sign exists.

A digital thermometer 67 feeds an abnormal temperature such as a temperature above 99.1° F. through its interface to microprocessor unit 70. The MPU 70 will go into an alert routine to indicate a temperature problem and sound alarm beeper 83. In operation, MPU 70 compares preprogrammed danger temperature such as for example a preset temperature between 99° and 100° F. with the sensed temperature. When the sensed temperature is equal to the danger temperature, the processor goes into the alert routine.

Each of the microphones 80 and 81 have limited band widths for sensing the respiration and the sound activity of the heart in order to determine cardiac and respiratory status. The limited band width is designed to be selective in the range of sound that each of the microphones pick up. Each microphone puts out an analog signal which is converted into digital data by the analog to digital converter 76 and 77 so that MPU 70, Which is digital, can analyze the data. In this application, MPU 70 has the dominent role in data transfer operations. The processor performs a required signal averaging shaping or other linear or non-linear operations to deliver the desired type of information. The processor begins analysis by filtering out ambient noises through a technique called digital filtering. Processor 70 then separates the cardiac and respiratory sound data if only one microphone is involved. In the case of two microphones MPU 70 analyzes each segment of digital information representing and cardiac and respiration status. In one embodiment, the processor 70 analyzes one vital sign for two consecutive minutes before switching to a further vital sign. If the apparatus is to be used for monitoring adults, the respiration rate is generally about 20 per minutes whereas in a baby the respiratory rate is about 30. The temperature of an adult and a baby is approximately the same. The pulse rate of a child at birth is approximately 140 beats per minute, and after 48 hours the pulse rate drops to about 110. The average pulse rate of an adult is about 70 beats per minute. The instructions of the program are put into ROM 71 for either an adult or a baby so that a series of routines are performed by the circuit of FIG. 2 in the microprocessor.

Figure 2:
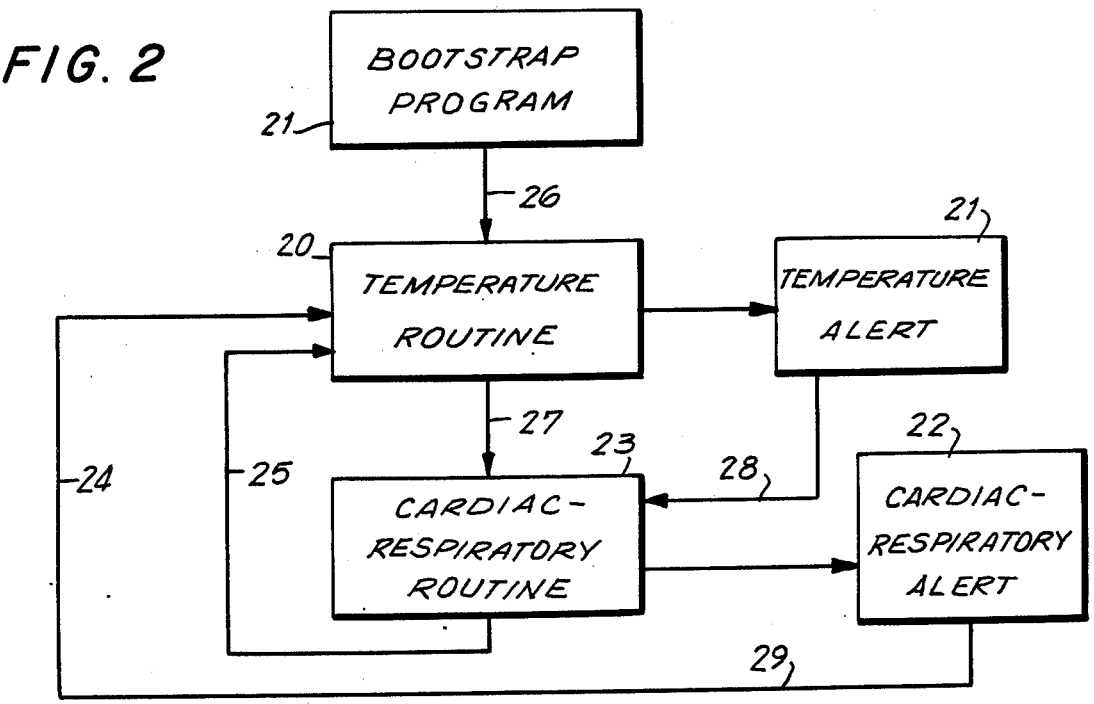
FIG. 2 is an electronic block diagram illustrating one program of the invention.

FIG. 2 is an electrical block diagram of a typical unit routine which senses abnormal vital signs in a patient's temperature, respiration and heart rate. When belt 10 is closed, bootstrap program 21 resets itself and initiates both the temperature routine 20 via connection 26, and cardiac-respiratory routine 23 via line 27. The output of temperature routine 20 is connected to a temperature alert 21 and the output of cardiac respiratory routine 23 is coupled to a C.R. alert 22. Both routines and alerts are interconnected via lines 24, 25, 28 and 29. The following routines are processed:

1. Breathing problem
   A. Too fast
   B. Too slow or no breathing
   C. Irregular breathing
2. Heart rate problem
   A. Too fast B. Too slow or no beating
C. Irregular heart beat
3. Temperature problem
A. Too high
B. Too low
C. Too rapid a temperature change Microprocessor unit 70 can indicate one or more problems simultaneously. The unit will preferably have a fail-safe trigger by requiring about six consecutive seconds of danger routine before going into an alert routine.

The unit will record each vital sign in memory preferably every hour for a future readout. In order to request processor unit 70 to put out its memory contents such as the hourly vital sign reading, an interrupt button is depressed which causes the processor to go into a sub-routine that outputs its memory contents stored in RAM 72.

In order to start up the unit, the user closes the belt buckle which turns the unit on and resets it. The unit then goes into a bootstrap routine which initiates the processor and puts the processor into a self-analysis program which checks the memory and other functions. This routine lasts approximately two minutes until the processor goes to normal operation, after the readings of the vital signs have stabilized.

Another possible format in which the normal parameters are not preprogrammed in advance is to allow the unit to record the data initially and use this initial data as a reference in the analysis. If a future sampling differs by more than a preset deviation such as one or two percent of the original reference points, the unit will go into a sub-routine alert.

For example, if a reference temperature is 98.6° F. then a difference of more than 0.98° F. may be considered a danger and the unit will go into a sub-routine alert.

The unit of the present invention can be used by adults, children or animals. It may employ regular batteries or rechargable batteries which are accessable through housing 17. A beeper alarm is provided in the monitor and can be amplified by a pick-up microphone placed a few feet from the patient to increase the volume of the beeper sound.

If the unit is to be used for sampling the vital signs of animals such as horses, a small pin that contains a thermister probe for temperature measurement can be inserted painlessly under the skin of the animal. Horses have a thick and hairy skin so that such a probe is needed to sense the temperature.

If the unit is to be used as a monitor for babies or small children, it can be easily attached around the waist of the child while the child is taking a nap or sleeping during the night so that baby's vital signs can be continuously monitored. In an abnormality, such as in the beginning of a crib death situation, the unit will sound a loud beeper and allow a nurse or parent to apply artificial resuscitation to the child within the next few minutes before brain damage sets in.

While only a few embodiments of the present invention have been shown and described, it will be obvious to those skilled in the art that many changes and modifications may be made thereunto without departing from the spirit and scope of the invention.

What is claimed is:

1. A monitoring system for measuring the vital signs such as temperature, respiration and heart beat of a patient comprising:
    a housing designed for body contact with the skin of the patient;
    means for securing said housing on a patient's body;
    clock timing means disposed in said housing for generating time based signals;
    logic means connected to said clock timing means and being responsive to said time based signals for selecting the proper combinations of said time based signals;
    a temperature sensor coupled to sid logic means and disposed on said housing for measuring the body temperature of the human subject;
    microphone means coupled to said logic means and mounted in said housing for detecting respiratory and cardiac sounds;
    solid state memory means having coded information temperature, respiration and cardiac signals and coupled to said logic means for sequencing said logic means to take a plurality of temperature, cardiac and respiratory readings at a preset real time and to compare said measured readings with said coded information signals;
    data storage means for sequentially recording each of the stabilized temperature, respiration and cardiac readings that were measured; and
    display means on said housing responsive to said solid state memory means and said logic means for indicating the magnitude of the temperature, respiration and heart beat of the patient.

2. The monitoring system as recited in claim 1, additionally comprising alarm means for indicating abnormalities in the vital signs of the patient, which includes an alarm circuit coupled to said logic means and responsive to said solid state memory means.

3. The monitoring system as recited in claim 1 wherein said microphone means comprises a first microphone for measuring heart beat, a bandwidth amplifier, the input of which is coupled to the output of said first microphone and an analogue to digital converter, the input of which is coupled to the output of said amplifier and the output of which is coupled to said logic means, and
    a second microphone for measuring respiration, a bandwidth amplifier, the input of which is coupled to the output of said second microphone, and an analogue to digital converter, the input of which is coupled to the output of said amplifier and the output of which is coupled to said logic means.

4. The monitoring system as recited in claim 1 wherein said logic means comprises a microprocessor, said temperature sensor comprises a digital thermometer, said solid state memory means comprises a ROM and said data storage means comprises a RAM.

5. The monitoring system as recited in claim 1 wherein said display means comprises a first LED pulse display, a second LED temperature display and a third LED respiration display.

6. The monitoring system as recited in claim 1, wherein said means for securing includes a belt having couplings on each end thereof connecting said belt to said housing, and switch means mounted in said couplings for turning on and resetting said logic means in response to a connection to said housing. pg,22

7. The monitoring system as recited in claim 6 wherein said belt includes an induction coil disposed substantially along its length, having outlet terminals on at least one coupling end thereof connected to said housing, and a second induction coil disposed in close proximity with said belt coil, said second coil having a transformer mounted on one end for connection to a conventional power source, so as to impart an induced voltage to said belt coil.

* * * * *

UNITED STATES PATENT OFFICE
CERTIFICATE OF CORRECTION

Patent No. 4,129,125            Dated December 12, 1978

Inventor(s) Lester et al.

It is certified that error appears in the above-identified patent and that said Letters Patent are hereby corrected as shown below:

Column 1, line 6, delete "state" and substitute therefor --states--; Col. 1, line 10, after "answer" insert --as--; Col. 1, line 38, delete "an" and substitute therefor --and --; Col. 1, line 56, delete "dealth" and substitute therefor --dealt--. Column 2, line 66, delete "inducation" and substitute therefor --induction--. Column 5, line 8, delete "preferably" and substitute therefor --preferable--; Col. 5, line 35, delete "the". Column 6, line 26, delete "Which" and substitute therefor --which--. Column 8, line 8, delete "sid" and substitute therefor --said--; Col. 8, line 58, delete "pg 22".

Signed and Sealed this

Twentieth Day of March 1979

[SEAL]

Attest:

RUTH C. MASON
*Attesting Officer*

DONALD W. BANNER
*Commissioner of Patents and Trademarks*